US012313740B1

United States Patent
Larocca et al.

(10) Patent No.: US 12,313,740 B1
(45) Date of Patent: May 27, 2025

(54) PHASE DELAY ULTRASOUND FOR STEERED ULTRASOUND BEAM

(71) Applicant: Meta Platforms Technologies, LLC, Menlo Park, CA (US)

(72) Inventors: Francesco Larocca, Kirkland, WA (US); Anton Andreevich Shkel, Aliso Viejo, CA (US); Sachin Talathi, Snoqualmie, WA (US); Ning Lu, Redmond, WA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 234 days.

(21) Appl. No.: 18/073,995

(22) Filed: Dec. 2, 2022

(51) Int. Cl.
*G01S 15/89* (2006.01)
*A61B 8/00* (2006.01)
*G10K 11/34* (2006.01)

(52) U.S. Cl.
CPC ........ *G01S 15/8915* (2013.01); *A61B 8/4483* (2013.01); *G10K 11/346* (2013.01)

(58) Field of Classification Search
None
See application file for complete search history.

(56) References Cited

U.S. PATENT DOCUMENTS

| 3,948,248 | A | * | 4/1976 | Zuckerman | A61B 8/10 600/463 |
| 9,931,245 | B2 | | 4/2018 | Romano et al. | |
| 11,281,014 | B2 | | 3/2022 | Hughes et al. | |
| 11,346,943 | B1 | | 5/2022 | Scally et al. | |
| 11,526,018 | B2 | | 12/2022 | Senkal et al. | |
| 2004/0122316 | A1 | * | 6/2004 | Satoh | G01S 7/52047 600/437 |
| 2013/0172752 | A1 | | 7/2013 | Hu et al. | |
| 2016/0100822 | A1 | * | 4/2016 | Kim | A61B 8/14 600/472 |
| 2016/0157828 | A1 | * | 6/2016 | Sumi | G01N 29/46 702/189 |
| 2019/0129026 | A1 | * | 5/2019 | Sumi | A61B 6/00 |

FOREIGN PATENT DOCUMENTS

| CN | 109195717 B | * | 3/2021 | ........... B06B 1/0207 |
| CN | 115047465 A | * | 9/2022 | ......... G01S 15/8915 |
| EP | 3646956 A1 | * | 5/2020 | ........... B06B 1/0629 |

OTHER PUBLICATIONS

Sun S., et al., "Eye-Tracking Monitoring Based on PMUT Arrays," Journal of Microelectromechanical Systems, Feb. 2022, vol. 31, No. 1, pp. 45-53.
Sun S., et al., "MEMS Ultrasonic Transducers for Safe, Low-Power and Portable Eye-Blinking Monitoring," Microsystems & Nanoengineering, Jun. 13, 2022, vol. 8:63, 14 pages.

* cited by examiner

*Primary Examiner* — Rodney E Fuller
(74) *Attorney, Agent, or Firm* — Greenberg Traurig, LLP

(57) ABSTRACT

An ultrasound activation signal is received from ultrasound driving logic. A phase delay module of an ultrasound module generates phase-differentiated drive signals. The phase-differentiated drive signals are driven onto an array of ultrasound transducers to generate a steered ultrasound beam.

20 Claims, 6 Drawing Sheets

PHASE DELAY ULTRASOUND FOR STEERED ULTRASOUND BEAM

TECHNICAL FIELD

This disclosure relates generally to sensing, and in particular to ultrasound sensing.

BACKGROUND INFORMATION

Ultrasound transducers have historically been used for imaging and sensing applications. In some contexts, more than one ultrasound transducer is included in an imaging or sensing application. However, increasing the number of ultrasound transducers deployed into a system also increases the complexity of driving the ultrasound transducers and routing control signals to the ultrasound transducers.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Figure 1A:
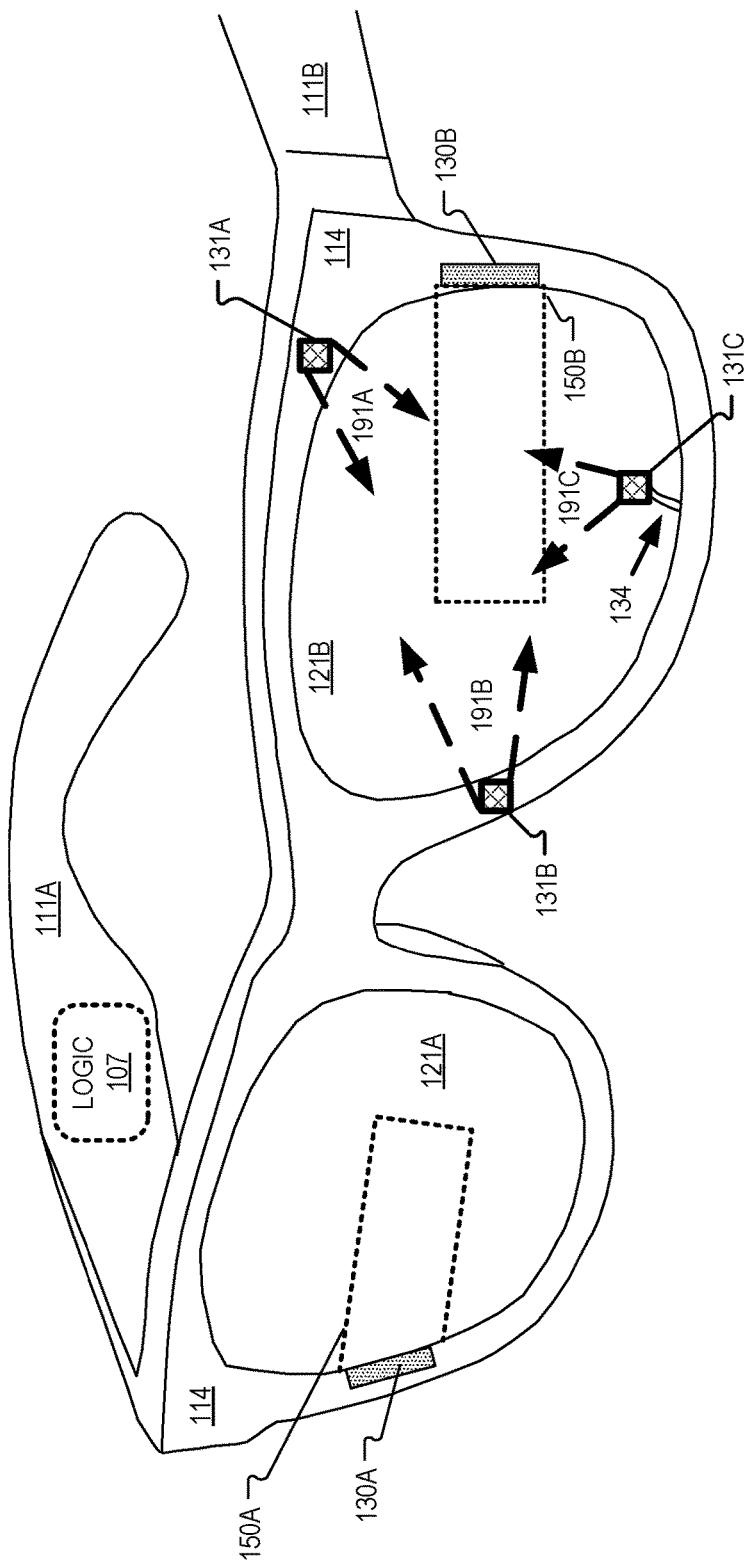
FIG. 1A illustrates a head mounted display (HMD) that may include a near-eye system, in accordance with aspects of the disclosure.

Embodiments of steering ultrasound beams with phase delay systems and techniques are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In some implementations of the disclosure, the term "near-eye" may be defined as including an element that is configured to be placed within 50 mm of an eye of a user while a near-eye device is being utilized. Therefore, a "near-eye optical element" or a "near-eye system" would include one or more elements configured to be placed within 50 mm of the eye of the user.

In aspects of this disclosure, the term "transparent" may be defined as having greater than 90% transmission of light. In some aspects, the term "transparent" may be defined as a material having greater than 90% transmission of visible light.

Ultrasound is defined as sound waves having frequencies above 20 kHz. Ultrasound frequencies may range for 20 kHz to 4 GHz, for example. In some implementations of the disclosure, the ultrasound frequencies are between 40 kHz and 2 MHz.

Discrete ultrasound transducers can be used for imaging and sensing techniques to sense a target from multiple angles. Additionally, a closely spaced group of ultrasound transducers can achieve ultrasound beam steering by being driven as a phased array where the drive signals on particular ultrasound transducers have different phases. This systems may be referred to as phased array ultrasound transducers. Yet, for phased array ultrasound transducers, each ultrasound transducer in the phased array is individually addressable, which adds complexity to routing traces to drive the individual ultrasound transducers and limits the contexts that the ultrasound module can be deployed in.

In a context such as eye-tracking, more than one phased array ultrasound transducers may be advantageous to increase the accuracy of tracking an eye position. However, in the context of head mounted devices, the space for Input/Output (IO) connections and associated electrical routing for each ultrasound transducers is particularly limited, especially when multiple phased array ultrasound transducers are utilized in an eye-tracking system.

In implementations of the disclosure, an ultrasound module includes an array of ultrasound transducers and a phase delay module configured to drive each of the ultrasound transducers with phase-differentiated drive signals. The phase delay module may be local to the array of ultrasound transducers. In some implementations, the phase delay module is co-located with the ultrasound transducers in the array. The phase delay module may be included in the same chip package as the ultrasound transducers, in some implementations. This phase delay module may allow for a drastic reduction in routing of IO lines. For example, a conventional phased array ultrasound module may require 10-18 IO lines, depending on the number of transducers in the phase array. In contrast, implementations of the disclosure may require only two or three IO lines to be routed to the ultrasound module while still achieving beam forming from the ultrasound module to steer the ultrasound beam to a particular target with a particular beam shape.

In some implementations of the disclosure, the ultrasound module is disposed on a transparent (or semi-transparent) optical element of a head mounted device that is in the field-of-view (FOV) of a user of the head mounted device. In this particular context, reducing the routing to the ultrasound module may be particularly valuable. In some implementations, the ultrasound transducers in the ultrasound module are transparent. These and other embodiments are described in more detail in connection with FIGS. 1A-5.

FIG. 1A illustrates a head mounted display (HMD) 100 that may include a near-eye system, in accordance with aspects of the present disclosure. HMD 100 includes frame 114 coupled to arms 111A and 111B. Lens assemblies 121A and 121B are mounted to frame 104. Lens assemblies 121A and 121B may include a prescription lens matched to a particular user of HMD 100. The illustrated HMD 100 is configured to be worn on or about a head of a wearer of HMD 100.

In the HMD 100 illustrated in FIG. 1A, each lens assembly 121A/121B includes a display waveguide 150A/150B to direct image light generated by displays 130A/130B to an eyebox region for viewing by a user of HMD 100. Displays 130A/130B may include a beam-scanning display that includes a scanning mirror, for example. While HMD 100 is illustrated as a head mounted display, implementations of the disclosure may also be utilized on head mounted devices (e.g. smartglasses) that don't necessarily include a display.

Lens assemblies 121A and 121B may appear transparent to a user to facilitate augmented reality or mixed reality to enable a user to view scene light from the environment around them while also receiving image light directed to their eye(s) by, for example, waveguides 150. Lens assemblies 121A and 121B may include two or more optical layers for different functionalities such as display, eye-tracking, and optical power. In some embodiments, image light from display 130A or 130B is only directed into one eye of the wearer of HMD 100. In an embodiment, both displays 130A and 130B are used to direct image light into waveguides 150A and 150B, respectively.

Frame 114 and arms 111 may include supporting hardware of HMD 100 such as processing logic, wired and/or wireless data interface for sending and receiving data, graphic processors, and one or more memories for storing data and computer-executable instructions. The processing logic may include circuitry, logic, instructions stored in a machine-readable storage medium, ASIC circuitry, FPGA circuitry, and/or one or more processors. In one embodiment, HMD 100 may be configured to receive wired power. In one embodiment, HMD 100 is configured to be powered by one or more batteries. In one embodiment, HMD 100 may be configured to receive wired data including video data via a wired communication channel. In one embodiment, HMD 100 is configured to receive wireless data including video data via a wireless communication channel.

FIG. 1A illustrates example ultrasound modules 131A, 131B, and 131C (collectively referred to as ultrasound modules 131) that are disposed in different positions on HMD 100. In different implementations, more or fewer ultrasound modules 131 may be implemented in a head mounted device. Ultrasound module 131A generates a steered ultrasound beam 191A directed to an eyebox region that an eye of a wearer of HMD 100 will occupy. Ultrasound module 131B and ultrasound module 131C may also generate steered ultrasound beams 191B and 191C directed to the eyebox region that an eye of a wearer of HMD 100 will occupy. Ultrasound modules 131A and 131B are disposed on or in frame 114 of HMD 100. Ultrasound modules 131C is disposed in or on lens assembly 121B. Lens assembly 121B may be transparent or semi-transparent so that a wearer of HMD 100 can view their external environment through lens assembly 121B.

Ultrasound driving logic 107 is illustrated as included in arm 111A of HMD 100, although ultrasound driving logic 107 may be disposed in the frame 114 or arms 111 of HMD 100. Ultrasound driving logic 107 is configured to drive one or more ultrasound modules 131 to direct steered ultrasound beams 191 to the eyebox region. Ultrasound driving logic 107 may be coupled to drive ultrasound module 131C by way of traces/conductors 134. Traces 134 may be transparent, semi-transparent, or opaque. Traces 134 may include indium tin oxide (ITO) or copper.

Figure 1B:
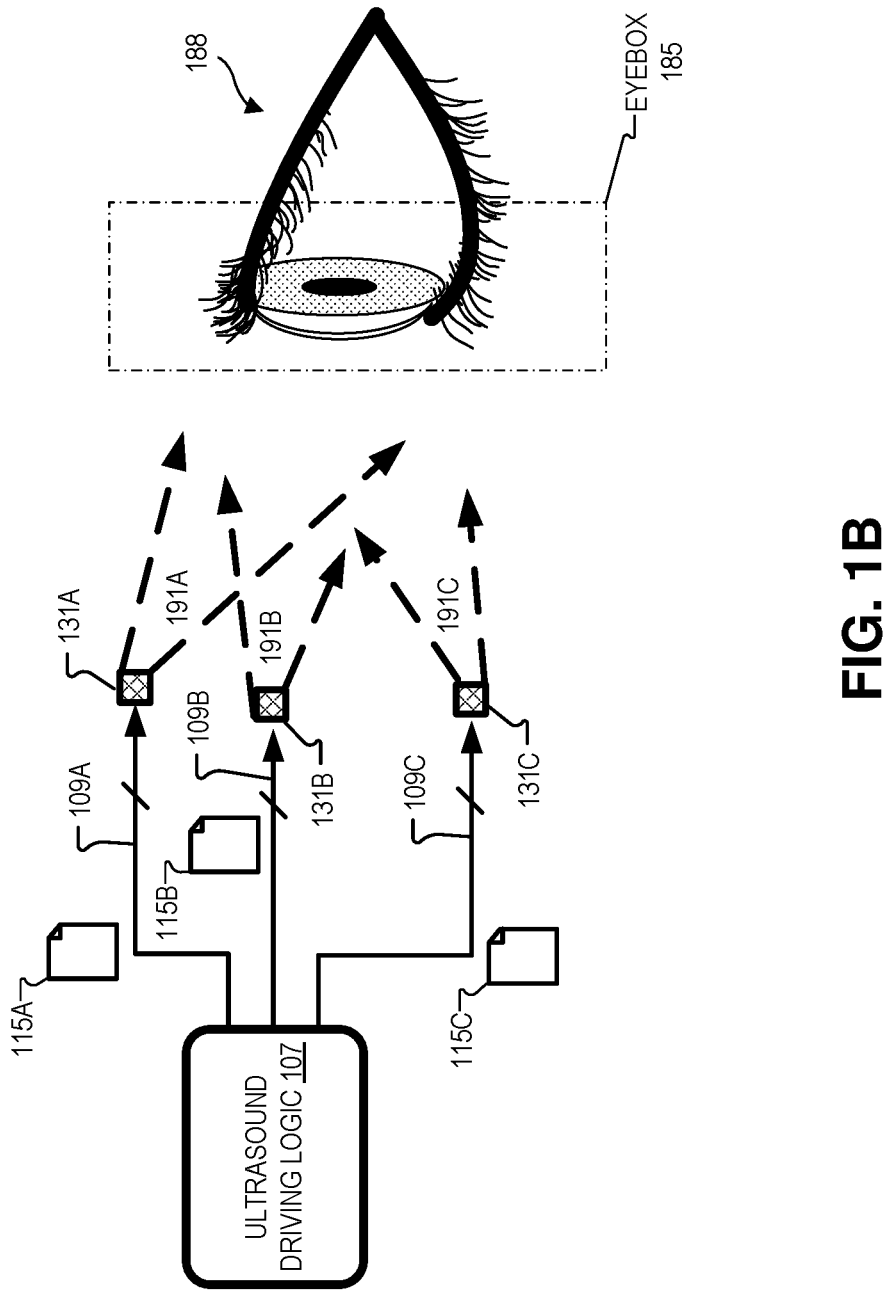
FIG. 1B illustrates ultrasound driving logic transmitting activation signals to ultrasound modules, in accordance with aspects of the disclosure.

FIG. 1B illustrates a near-eye system 160 having ultrasound driving logic 107 transmitting activation signals to ultrasound modules 131, in accordance with implementations of the disclosure. Ultrasound driving logic 107 may be included in a central processing logic of HMD 100 or be a stand-alone processor. Ultrasound driving logic 107 drives an activation signal 115A to ultrasound module 131A by way of communication channel 109A. Ultrasound driving logic 107 also drives activation signal 115B and 115C to ultrasound modules 131B and 131C by way of communication channel 109B and 109C, respectively. Communication channels 109 may include two conductors. The ultrasound modules 131 are configured to generate steered ultrasound beams 191 directed to eye 188 that occupies eyebox region 185.

Figure 2:
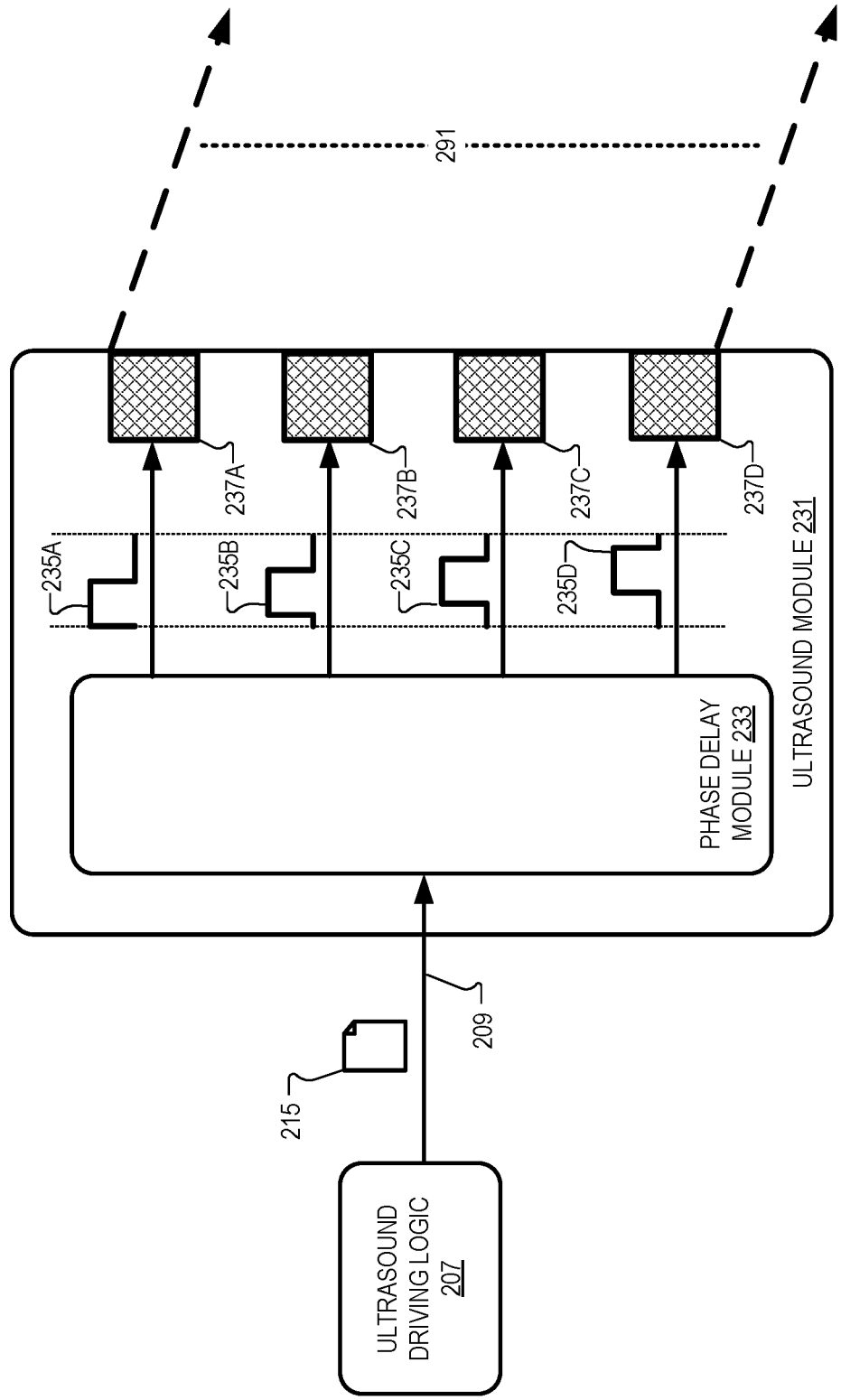
FIG. 2 illustrates an example ultrasound module that includes a phase delay module and an array of ultrasound transducers, in accordance with aspects of the disclosure.

FIG. 2 illustrates an example ultrasound module 231 that includes a phase delay module 233 and an array of ultrasound transducers 237A-237D, in accordance with implementations of the disclosure. Ultrasound module 131 may include the features of ultrasound module 231. FIG. 2 illustrates four ultrasound transducers 237A, 237B, 237C, and 237D (collectively referred to as ultrasound transducers 237) although different numbers of ultrasound transducers may be included in ultrasound module 231. For example, ultrasound module 231 may include eight, twelve, or sixteen ultrasound transducers. In some implementations, the ultrasound transducers 237 include piezoelectric micromachine ultrasound transducers (PMUTs) or capacitive micromachine ultrasound transducers (CMUTs).

Phase delay module 233 receives activation signal 215 from ultrasound driving logic 207 by way of communication channel 209. Phase delay module 233 is configured to drive each of the ultrasound transducers 237 with phase-differentiated drive signals 235. Phase delay module 233 may be co-located with ultrasound transducers 237 in ultrasound module 231. In some implementations, "co-located" is defined as within 5 mm. Phase delay module 233 may be co-located with ultrasound transducers 237 in a same chip package. In the specific illustration of FIG. 2, phase delay module 233 drives ultrasound transducer 237A with phase-differentiated drive signal 235A, drives ultrasound transducer 237B with phase-differentiated drive signal 235B, drives ultrasound transducer 237C with phase-differentiated drive signal 235C, and drives ultrasound transducer 237D with phase-differentiated drive signal 235D. Phase-differentiated drive signals 235 vary in phase with respect to each other or with respect to at least one of the other phase-differentiated drive signals 235. In the illustrated example of FIG. 2, phase-differentiated drive signal 235B is slightly delayed from phase-differentiated drive signal 235A, phase-differentiated drive signal 235C is slightly delayed from phase-differentiated drive signal 235B, and phase-differentiated drive signal 235D is slightly delayed from phase-differentiated drive signal 235C. The array of ultrasound transducers 237 is configured to generate a steered ultrasound beam 291 in response to receiving the phase-differentiated drive signals 235.

As illustrated in FIGS. 1A and 1B, an eye-tracking system may include more than one ultrasound module. In an implementation, more than one ultrasound modules are disposed in an optical element secured by a frame 114 of HMD 100. For example, ultrasound module 131C may be disposed in an optical element included in a lens assembly 121. More than one ultrasound module 131 may be included in the optical element. The one or more ultrasound modules may be disposed in a field of view of a user of the HMD 100. For example, FIG. 1A illustrates that ultrasound module 131C is included in lens assembly 121B and a user of HMD 100 may look through lens assembly 121 to view their surroundings in the external environment.

In some implementations, one or more the ultrasound modules 131/231 are transparent or at least partially transparent. This enhances the user experiences by reducing or eliminating noticeable occlusions in the field of view of the user. FIG. 1A illustrates ultrasound driving logic 107 as disposed in arm 111A of HMD 100 although the ultrasound driving logic 107 may be disposed in frame 114, in some implementations. In some implementations, conductors 134 are transparent and carry (transmit) activation signal 115/215 to ultrasound module 131C.

Figure 3:
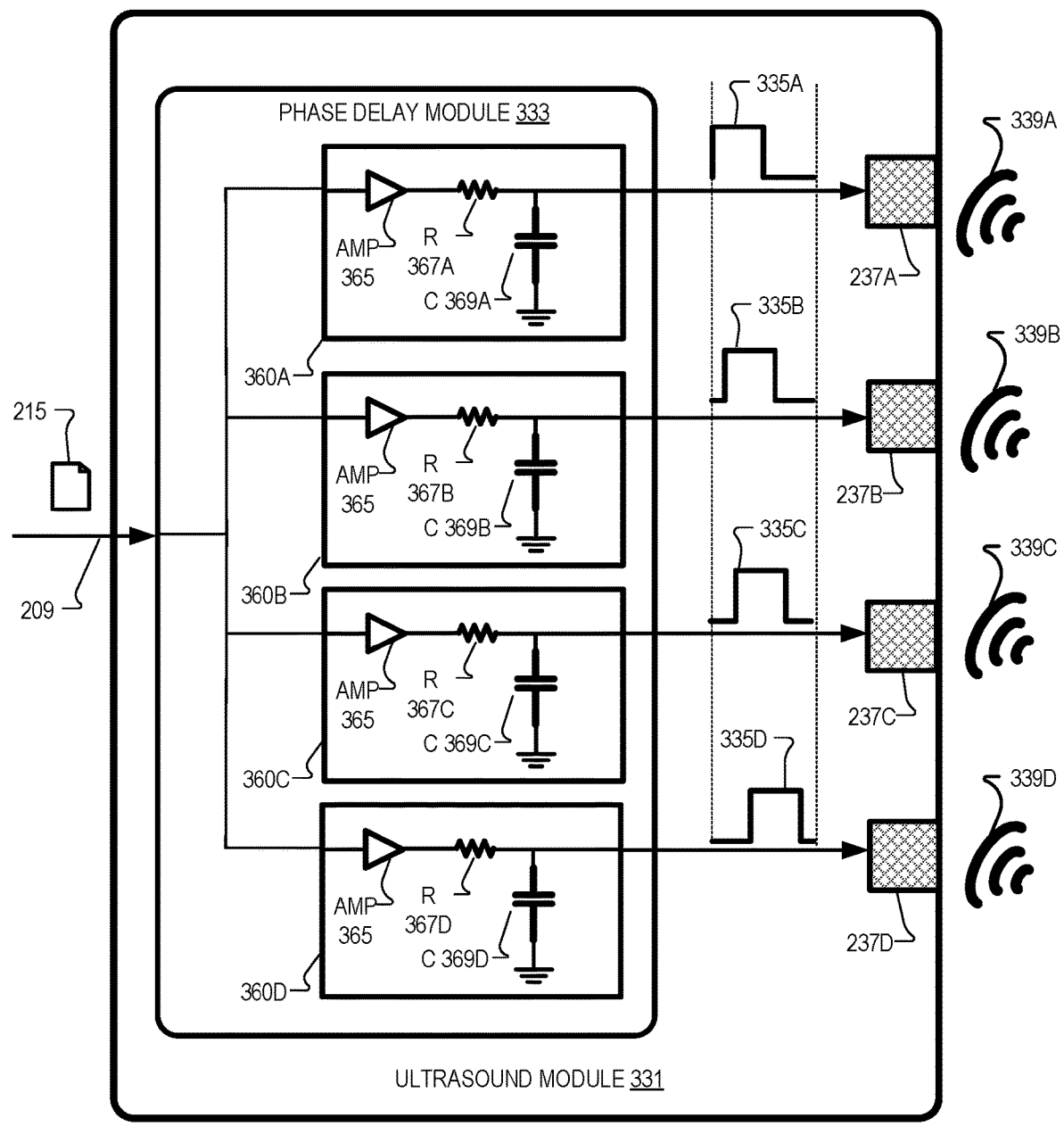
FIG. 3 illustrates an example phase delay module included in an ultrasound module that includes capacitive electrical components to generate phase-differentiated drive signals, in accordance with aspects of the disclosure.

FIG. 3 illustrates an example phase delay module 333 included in ultrasound module 331 that includes capacitive electrical components to generate phase-differentiated drive signals, in accordance with aspects of the disclosure. In FIG. 3, phase delay module 333 includes individual delay modules 360A, 360B, 360C, and 360D (collectively referred to as individual delay modules 360). In the illustrated implementation, each individual delay module 360 receives activation signal 215.

The example individual delay modules 360 includes an optional amplifier (AMP) 365, a resistive element, and a capacitive electrical component. In particular, individual delay module 360A includes amplifier (AMP) 365, a resistive element (R) 367A, and a capacitive electrical component (C) 369A; individual delay module 360B includes amplifier (AMP) 365, a resistive element (R) 367B, and a capacitive electrical component (C) 369B; individual delay module 360C includes amplifier (AMP) 365, a resistive element (R) 367C, and a capacitive electrical component (C) 369C; and individual delay module 360D includes amplifier (AMP) 365, a resistive element (R) 367D, and a capacitive electrical component (C) 369D. The resistive elements may be resistors and the capacitive electrical component may be capacitors. Varying the value of the resistive elements and/or the capacitive electrical component affects the RC time constant of the delay module 360A and thus the selection of the value of the resistive element and/or the capacitive electrical component varies the phase of the phase-differentiated drive signals 335. In some implementations, the capacitive electrical component 369 of the individual delay modules 360 may vary in capacitance to generate the phase-differentiated signals 335. In the illustration of FIG. 3, the capacitive electrical component 369 is coupled to an input of the corresponding ultrasound transducer 237. In other implementations, the particular electrical arrangement of a capacitive circuit may be configured differently while still adjusting the phase of the phase-differentiated drive signals 335.

Ultrasound transducer 237A generates an individual ultrasound beam 339A in response to phase-differentiated drive signal 335A; ultrasound transducer 237B generates an individual ultrasound beam 339B in response to phase-differentiated drive signal 335B; ultrasound transducer 237C generates an individual ultrasound beam 339C in response to phase-differentiated drive signal 335C; and ultrasound transducer 237D generates an individual ultrasound beam 339D in response to phase-differentiated drive signal 335D. The constructive and destructive interference of individual ultrasound beams 339A, 339B, 339C, and 339D combine to form the steered ultrasound beam 291, of FIG. 2.

Figure 4:
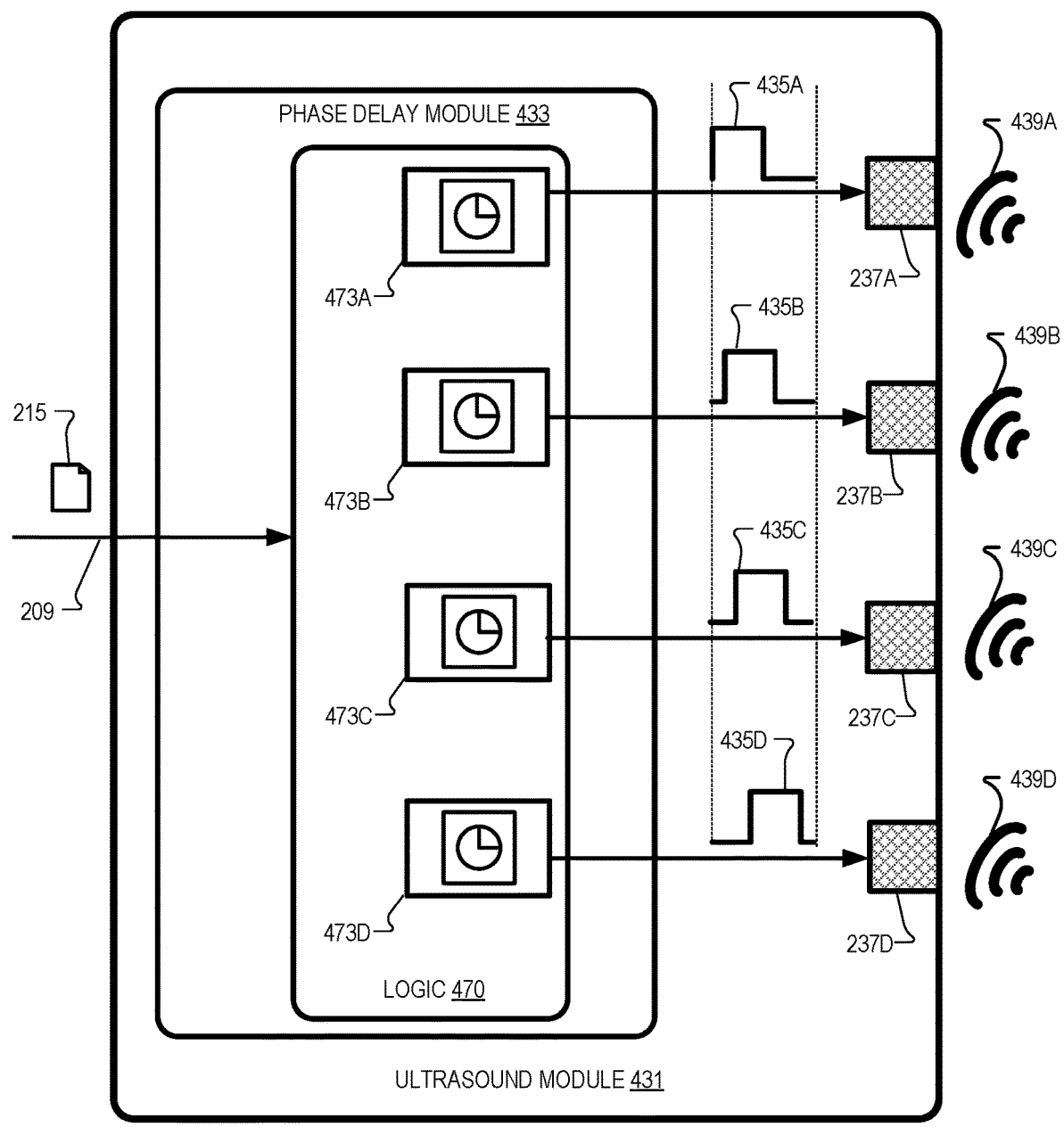
FIG. 4 illustrates an example phase delay module in an ultrasound module that includes processing logic that generates phase-differentiated drive signals, in accordance with aspects of the disclosure.

FIG. 4 illustrates an example phase delay module 433 in ultrasound module 431 that includes processing logic 470 that generates phase-differentiated drive signals, in accordance with aspects of the disclosure. In FIG. 4, processing logic 470 includes example timer modules 473A, 473B, 473C, and 473D (collectively referred to as timer modules 473). When processing logic 470 receives activation signal 215, processing logic 470 may set and start timer modules 473A with different timer counts to generate phase-differentiated drive signals 435A, 435B, 435C, and 435D as outputs of the timer modules 473A, 473B, 473C, and 473D, respectively. Hence, timers may be started when a count for timers for each ultrasound transducer 237 are incremented or decremented in response to activation signal 215.

Ultrasound transducer 237A generates an individual ultrasound beam 439A in response to phase-differentiated drive signal 435A; ultrasound transducer 237B generates an individual ultrasound beam 439B in response to phase-differentiated drive signal 435B; ultrasound transducer 237C generates an individual ultrasound beam 439C in response to phase-differentiated drive signal 435C; and ultrasound transducer 237D generates an individual ultrasound beam 439D in response to phase-differentiated drive signal 435D. The constructive and destructive interference of individual ultrasound beams 439A, 439B, 439C, and 439D combine to form the steered ultrasound beam 291, of FIG. 2.

Activation signal 215 may be an analog or digital message. If activation signal 215 is digital, logic 470 may set different timer counts for the timer modules 473 in response to the digital message included in activation signal 215. In this way, the steered ultrasound beam generated by individual ultrasound beams 439A, 439B, 439C, and 439D may be dynamically changed by sending digital messages with different content. Put more generally, phase delay module 433 may modulate phase-differentiated signals 435 in response to a digital message in activation signal 215. Thus, the shape and direction of the steered ultrasound beam 291 may be dynamically configurable based on the digital message included in activation signal 215.

FIG. 4 illustrates a timer-based implementation of processing logic 470, although other implementations may be used to vary the phase of phase-differentiated drive signals 435. Any combination of analog or digital components to generate phase delays may be used. By way of example and not limitation, transistor delay circuits, "555 timers", or op-amp delay circuits may be used as delay circuitry in processing logic 470. Processors or application-specific integrated circuits (ASIC) may be used to implement processing logic 470.

In some implementations, the configuration of processing logic 470 is fixed in hardware. In other implementations, the configuration of processing logic 470 is dynamically reconfigurable in response to an analog or digital activation signal 215. In the dynamically reconfigurable implementations, the shape and/or direction of steered ultrasound beam 291 can be changed by driving different phase-differentiated drive signals 435 onto ultrasound transducers 237.

Figure 5:
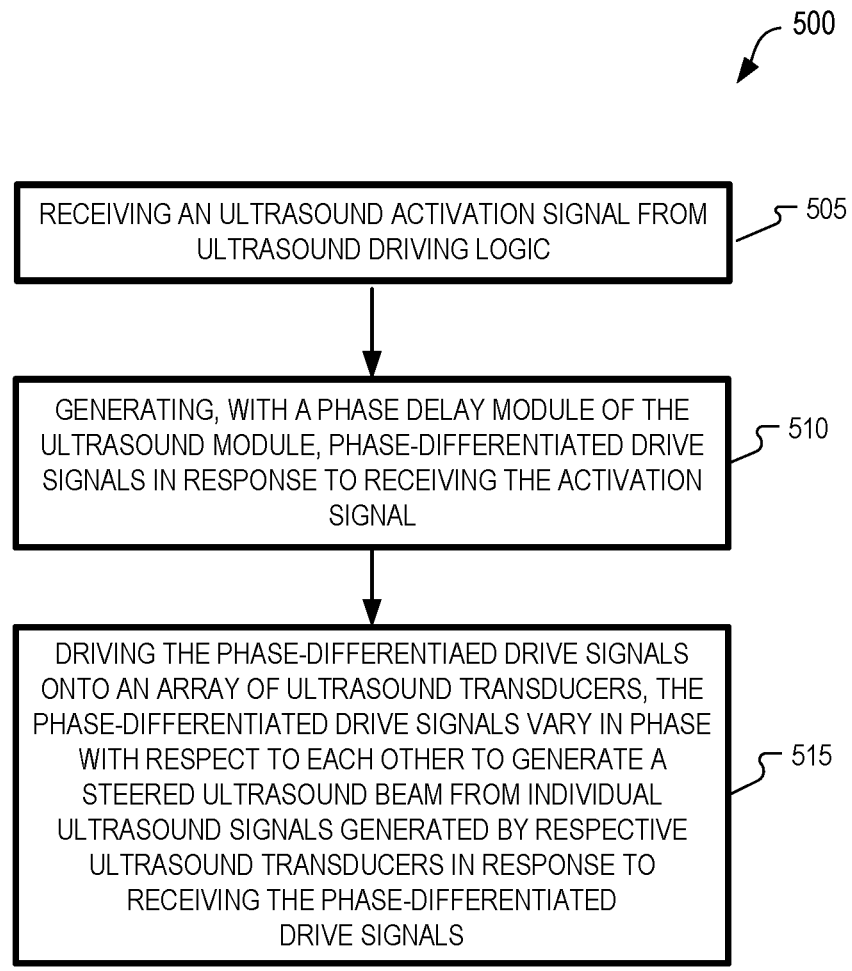
FIG. 5 illustrates a flow chart of an example process of ultrasound beam forming with phase-differentiated drive signals, in accordance with aspects of the disclosure.

FIG. 5 illustrates a flow chart of an example process 500 of ultrasound beam forming with phase-differentiated drive signals, in accordance with aspects of the disclosure. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In process block 505, an ultrasound activation signal is received from ultrasound driving logic.

In process block 510, a phase delay module generates phase-differentiated drive signals in response to receiving the ultrasound activation signal. The phase delay module is included in an ultrasound module.

In process block 515, the phase-differentiated drive signals are driven onto an array of ultrasound transducers. The phase-differentiated drive signals vary in phase with respect to each other to generate a steered ultrasound beam propagating to an eyebox region from individual ultrasound signals generated by respective ultrasound transducers in response to receiving the phase-differentiated drive signals. The phase delay module is co-located in a same chip-package as the array of ultrasound transducers.

In some implementations, the phase delay module includes a capacitive electrical component coupled to an input of each of the ultrasound transducers in the array of ultrasound transducers and the capacitive electrical component coupled to the inputs of the ultrasound transducers vary in capacitance to generate the phase-differentiated drive signals.

In some implementations, the ultrasound activation signal includes a digital message and the phase delay module modulates the phase-differentiated drive signals in response to the digital message.

Embodiments of the invention may include or be implemented in conjunction with an artificial reality system. Artificial reality is a form of reality that has been adjusted in some manner before presentation to a user, which may include, e.g., a virtual reality (VR), an augmented reality (AR), a mixed reality (MR), a hybrid reality, or some combination and/or derivatives thereof. Artificial reality content may include completely generated content or generated content combined with captured (e.g., real-world) content. The artificial reality content may include video, audio, haptic feedback, or some combination thereof, and any of which may be presented in a single channel or in multiple channels (such as stereo video that produces a three-dimensional effect to the viewer). Additionally, in some embodiments, artificial reality may also be associated with applications, products, accessories, services, or some combination thereof, that are used to, e.g., create content in an artificial reality and/or are otherwise used in (e.g., perform activities in) an artificial reality. The artificial reality system that provides the artificial reality content may be implemented on various platforms, including a head-mounted display (HMD) connected to a host computer system, a standalone HMD, a mobile device or computing system, or any other hardware platform capable of providing artificial reality content to one or more viewers.

The term "processing logic" (e.g. ultrasound driving logic 107 or 207 or processing logic 470) in this disclosure may include one or more processors, microprocessors, multi-core processors, Application-specific integrated circuits (ASIC), and/or Field Programmable Gate Arrays (FPGAs) to execute operations disclosed herein. In some embodiments, memories (not illustrated) are integrated into the processing logic to store instructions to execute operations and/or store data. Processing logic may also include analog or digital circuitry to perform the operations in accordance with embodiments of the disclosure.

A "memory" or "memories" described in this disclosure may include one or more volatile or non-volatile memory architectures. The "memory" or "memories" may be removable and non-removable media implemented in any method or technology for storage of information such as computer-readable instructions, data structures, program modules, or other data. Example memory technologies may include RAM, ROM, EEPROM, flash memory, CD-ROM, digital versatile disks (DVD), high-definition multimedia/data storage disks, or other optical storage, magnetic cassettes, magnetic tape, magnetic disk storage or other magnetic storage devices, or any other non-transmission medium that can be used to store information for access by a computing device.

Network may include any network or network system such as, but not limited to, the following: a peer-to-peer network; a Local Area Network (LAN); a Wide Area Network (WAN); a public network, such as the Internet; a private network; a cellular network; a wireless network; a wired network; a wireless and wired combination network; and a satellite network.

Communication channels may include or be routed through one or more wired or wireless communication utilizing IEEE 802.11 protocols, short-range wireless protocols, SPI (Serial Peripheral Interface), I2C (Inter-Integrated Circuit), USB (Universal Serial Port), CAN (Controller Area Network), cellular data protocols (e.g. 3G, 4G, LTE, 5G), optical communication networks, Internet Service Providers (ISPs), a peer-to-peer network, a Local Area Network (LAN), a Wide Area Network (WAN), a public network (e.g. "the Internet"), a private network, a satellite network, or otherwise.

A computing device may include a desktop computer, a laptop computer, a tablet, a phablet, a smartphone, a feature phone, a server computer, or otherwise. A server computer may be located remotely in a data center or be stored locally.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An eye-tracking system for a head mounted device, the eye-tracking system comprising:
   ultrasound driving logic configured to transmit an activation signal;
   an optical element to be secured by a frame of the head mounted device;
   transparent conductors disposed on the optical element for carrying the activation signal; and
   an ultrasound module including:
      an array of ultrasound transducers, wherein the ultrasound transducers are transparent, and wherein the transparent ultrasound transducers are disposed in the optical element secured by a frame of the head mounted device; and
      a phase delay module configured to drive each of the ultrasound transducers with phase-differentiated drive signals in response to receiving the activation signal, wherein the array of ultrasound transducers is configured to generate a steered ultrasound beam directed to an eyebox region in response to receiving the phase-differentiated drive signals, the phase-differentiated drive signals varying in phase with respect to each other, and wherein the transparent conductors disposed on the optical element are coupled between the ultrasound driving logic and the ultrasound module.

2. The eye-tracking system of claim 1, wherein the phase delay module includes a capacitive electrical component coupled to an input of each of the ultrasound transducers, and wherein the capacitive electrical component coupled to the inputs of the ultrasound transducers vary in capacitance to generate the phase-differentiated drive signals.

3. The eye-tracking system of claim 1, wherein the activation signal includes a digital message, and wherein the phase delay module modulates the phase-differentiated drive signals in response to the digital message.

4. The eye-tracking system of claim 1 further comprising:
   a second ultrasound module including:
      a second array of second ultrasound transducers; and
      a second phase delay module configured to drive each of the second ultrasound transducers with second phase-differentiated drive signals, wherein the second array of second ultrasound transducers is configured to generate a second steered ultrasound beam directed to the eyebox region in response to receiving the second phase-differentiated drive signals, the second phase-differentiated drive signals varying in phase with respect to each other.

5. The eye-tracking system of claim 1, wherein the ultrasound module is disposed in a field of view of a user of the head mounted device.

6. The eye-tracking system of claim 4, wherein the second ultrasound transducers are transparent.

7. The eye-tracking system of claim 1, wherein the ultrasound driving logic is disposed in the frame or arms of the head mounted device.

8. The eye-tracking system of claim 1, wherein the array of ultrasound transducers includes between nine and sixteen ultrasound transducers.

9. The eye-tracking system of claim 1, wherein the ultrasound transducers in the array of ultrasound transducers include piezoelectric micromachine ultrasound transducers (PMUTs) or capacitive micromachine ultrasound transducers (CMUTs).

10. The eye-tracking system of claim 1, wherein the phase delay module is co-located in a same chip-package as the array of ultrasound transducers.

11. An ultrasound module comprising:
   an array of ultrasound transducers, wherein the ultrasound transducers are transparent; and
   a phase delay module co-located within 5 mm of the ultrasound transducers in the ultrasound module, the phase delay module configured to drive each of the ultrasound transducers with phase-differentiated drive signals in response to receiving an activation signal, wherein the array of ultrasound transducers is configured to generate a steered ultrasound beam in response to receiving the phase-differentiated drive signals, the phase-differentiated drive signals varying in phase with respect to each other.

12. The ultrasound module of claim 11, wherein the phase delay module includes a capacitive electrical component coupled to an input of each of the ultrasound transducers, and wherein the capacitive electrical component coupled to the inputs of the ultrasound transducers vary in capacitance to generate the phase-differentiated drive signals.

13. The ultrasound module of claim 11, wherein the activation signal includes a digital message, and wherein the phase delay module modulates the phase-differentiated drive signals in response to the digital message.

14. The ultrasound module of claim 11, wherein the phase delay module includes a timer for each of the ultrasound transducers, the timer for each of the ultrasound transducers starting in response to the activation signal, wherein the phase-differentiated drive signals are an output of the respective timer.

15. The ultrasound module of claim 11, wherein the ultrasound transducers are transparent.

16. The ultrasound module of claim 11, wherein the array of ultrasound transducers includes between nine and sixteen ultrasound transducers.

17. The ultrasound module of claim 11, wherein the ultrasound transducers in the array of ultrasound transducers include piezoelectric micromachine ultrasound transducers (PMUTs) or capacitive micromachine ultrasound transducers (CMUTs).

18. A method of ultrasound beam-forming for eye-tracking, the method comprising:
   receiving an ultrasound activation signal from ultrasound driving logic;
   generating, with a phase delay module of an ultrasound module, phase-differentiated drive signals in response to receiving the ultrasound activation signal; and
   driving the phase-differentiated drive signals onto an array of ultrasound transducers, wherein the phase-differentiated drive signals vary in phase with respect to each other to generate a steered ultrasound beam propagating to an eyebox region from individual ultrasound signals generated by respective ultrasound transducers in response to receiving the phase-differentiated drive signals, and wherein the ultrasound transducers are transparent,
   and wherein the phase delay module is co-located in a same chip-package as the array of ultrasound transducers.

19. The method of claim 18, wherein the phase delay module includes a capacitive electrical component coupled to an input of each of the ultrasound transducers in the array of ultrasound transducers, and wherein the capacitive electrical component coupled to the inputs of the ultrasound transducers vary in capacitance to generate the phase-differentiated drive signals.

20. The method of claim 18, wherein the ultrasound activation signal includes a digital message, and wherein the phase delay module modulates the phase-differentiated drive signals in response to the digital message.

* * * * *